(12) United States Patent
Hong et al.

(10) Patent No.: US 7,927,651 B2
(45) Date of Patent: Apr. 19, 2011

(54) BIOSENSOR HAVING NANO WIRE FOR DETECTING FOOD ADDITIVE MONO SODIUM GLUTAMATE AND MANUFACTURING METHOD THEREOF

(75) Inventors: Seung-Hun Hong, Seoul (KR); Byung-Yang Lee, Seoul (KR); Dong-Joon Lee, Seoul (KR)

(73) Assignees: Seoul National University Industry Foundation, Seoul (KR); Mitech Corporation, Gyeonggi-do (KR)

( * ) Notice: Subject to any disclaimer, the term of this patent is extended or adjusted under 35 U.S.C. 154(b) by 203 days.

(21) Appl. No.: 12/296,070

(22) PCT Filed: Apr. 4, 2007

(86) PCT No.: PCT/KR2007/001648
§ 371 (c)(1),
(2), (4) Date: Dec. 8, 2008

(87) PCT Pub. No.: WO2007/114650
PCT Pub. Date: Oct. 11, 2007

(65) Prior Publication Data
US 2009/0155816 A1    Jun. 18, 2009

(30) Foreign Application Priority Data

Apr. 4, 2006   (KR) .................. 10-2006-0030666
Apr. 2, 2007   (KR) .................. 10-2007-0032581

(51) Int. Cl.
*C23C 14/54* (2006.01)
(52) U.S. Cl. ..... 427/10; 427/2.11; 427/2.13; 435/287.1; 436/525; 436/149; 429/90
(58) Field of Classification Search .......... None
See application file for complete search history.

(56) References Cited

U.S. PATENT DOCUMENTS
6,528,020 B1    3/2003 Dai et al.
(Continued)

FOREIGN PATENT DOCUMENTS
JP    2006-024023    1/2006
(Continued)

OTHER PUBLICATIONS

Gruner, G: "Carbon nanotube transistors for biosensing applications" Analytical and Bioanalytical Chemistry, vol. 384, 2006, pp. 322-335.
Kannan Balasubramanian et al: "Biosensors based on carbon nanotubes" Analytical and Bioanalytical Chemistry, vol. 385, No. 3, 2006, pp. 452-468.
(Continued)

*Primary Examiner* — Nelson Yang
(74) *Attorney, Agent, or Firm* — Venable LLP; Michael A. Sartori; Ryan M. Flandro

(57) ABSTRACT

There is provided a biosensor capable of increasing a detecting sensitivity of a target substance of glutamate, by using a nano wire having excellent electrical characteristics and by immobilizing a receptor of glutamate to be detected on a substrate which is disposed between a nano wire and another nano wire and a method for manufacturing the same. The biosensor for detecting glutamate according to the present invention can be manufactured with an arrangement in which the nano wire is selectively arranged on a solid substrate in a matrix. Since this biosensor can prevent the degradation of the nano wire in the electrical characteristic, it can sensitively detect glutamate even through a small amount thereof is contained in a food so that it can be effectively used in detecting the food additive existing in the processed foodstuffs.

6 Claims, 2 Drawing Sheets

U.S. PATENT DOCUMENTS

| | | | |
|---|---|---|---|
| 2002/0117659 A1* | 8/2002 | Lieber et al. | 257/14 |
| 2002/0172963 A1 | 11/2002 | Kelley et al. | |
| 2003/0134433 A1 | 7/2003 | Gabriel et al. | |
| 2003/0146111 A1 | 8/2003 | Abel et al. | |
| 2004/0132070 A1 | 7/2004 | Star et al. | |
| 2004/0200734 A1 | 10/2004 | Co et al. | |
| 2005/0045875 A1 | 3/2005 | Lai et al. | |
| 2005/0244811 A1* | 11/2005 | Soundarrajan et al. | 435/4 |
| 2006/0021881 A1 | 2/2006 | Soundarrajan et al. | |
| 2009/0152598 A1* | 6/2009 | Baek et al. | 257/253 |

FOREIGN PATENT DOCUMENTS

| | | |
|---|---|---|
| KR | 10-2003-0014997 | 2/2003 |
| KR | 10-702531 B1 | 3/2007 |
| WO | WO-2007/001401 A2 | 1/2007 |

OTHER PUBLICATIONS

Korean Notice of Allowance, dated Oct. 31, 2008 issued in KR 10-2007-0032579.

Rege et al., "Enzyme-Polymer-Single Walled Carbon Nanotube Composites as Biocatalytic Films", Nano Letters, vol. 3, No. 6, pp. 829-832 (Apr. 2003).

Burmeister, J. J. et al: "Self-referencing ceramic-based multisite microelectrodes for the detection and elimination of interferences from the measurement of L-glutamate and other analytes." Analytical Chemistry, vol. 73, No. 5, Mar. 1, 2001, pp. 1037-1042.

Xu, Jing-Juan et al: "Analytical aspects of fet-based biosensors." Frontiers in Biosciencce: A Journal and Virtual Library, vol. 10, 2005, pp. 420-430.

* cited by examiner

BIOSENSOR HAVING NANO WIRE FOR DETECTING FOOD ADDITIVE MONO SODIUM GLUTAMATE AND MANUFACTURING METHOD THEREOF

TECHNICAL FIELD

The present invention relates to a biosensor for detecting glutamate using a nano wire and a method for manufacturing the same; and, more particularly, to a biosensor capable of increasing a detection sensitivity of a target substance of glutamate, by using a nano wire having excellent electrical characteristics and by immobilizing a receptor of glutamate to be detected on a substrate which is disposed between a nano wire and another nano wire and a method for manufacturing the same.

BACKGROUND ART

Nano-sized materials come into the limelight these days because of their excellent electrical, optical, and mechanical properties. The research that has been being so far progressed about the nano structure shows a possibility as advanced materials for the optical devices based on the new phenomenon like the quantum size effect. Particularly, in case of the nano wire, it is highlighted as the new optical device materials as well as a single electron tunneling device.

The carbon nanotube, as a typical example of the nano wire, is in a tubular form and has a structure in which one carbon atom is covalently bonded to other carbon atoms in hexagonal honeycomb structure. The diameter of the carbon nanotube is exceedingly small to a nano-scale. Particularly, this carbon nanotube is known as a perfect material which nearly does not have any defect among the existing materials and which has a remarkable characteristic in the mechanical property, the electrical selectivity, the field emission or the high-efficiency hydrogen storage.

Recently, high performance bimolecular sensors have been developed by using the nano wire like the carbon nanotube. The reason why the nano wire like the carbon nanotube is used for a biosensor is that a labeling for optical measurement is not required and a reaction can be created in the water phase without the deformation of a protein. That is, a fluorescent material, an isotope, or the like has been used for detecting the reaction results in a conventional biomolecule sensing method; however, the materials such as the fluorescence or the isotope are very harmful to the human body and the detection procedure is moreover complicate. If the electrical characteristic of the nano wire is used at the time of detection, it has an advantage that it is not harmful to health and it can exactly detect the reaction results.

However, in the conventional biosensor using the existing nano wire or the carbon nanotube, there is a problem in that the resistance increases, the electrical characteristic is degraded, and the detection sensitivity is also degraded consequently, especially in binding a material, which can directly react on the nano wire or the carbon nanotube, with a biomaterial. Moreover, there is a problem in that the electrical characteristic of each nano wire is transformed at the time of plating a polymer layer on a surface of the nano wire or directly immobilizing the biomaterial on the surface of the nano wire through a linker molecule.

Therefore, a demand for a high sensitivity biosensor, in which the electrical characteristic is not degraded, has increased with the excellent and convenient electrical characteristics of the nano wire.

Meanwhile, with the development of the food industry, the many kinds of processed foods appear recently. Accordingly, the kind and consumption of an additive used for the food expands more and more. The food additive is inevitably used for processing and preserving the foods; however, the secure of the safety should be austerely held in high repute, because the food additive itself, strictly speaking, is not a food ingredient and a little amount thereof is continuously taken through the foods for a lifetime. Even though general consumers have an interrogation or an anxiety about the food additive, most of them do not know whether what kinds of the foods have the food additive and how much the additive is safe for health. Therefore, a method for easily confirming whether there is the food additive in the foods is gradually required.

DISCLOSURE

Technical Problem

An embodiment of the present invention is directed to providing a biosensor having excellent electrical characteristic and a high detection sensitivity in detecting glutamate, especially a food additive of monosodium L-glutamate.

Other objects and advantages of the present invention can be understood by the following description, and become apparent with reference to the embodiments of the present invention. Also, it is obvious to those skilled in the art of the present invention that the objects and advantages of the present invention can be realized by the means as claimed and combinations thereof.

Technical Solution

In accordance with an aspect of the present invention, there is provided a biosensor for detecting glutamate, including: a solid substrate; at least one signal transducer which is arranged in a matrix and has nano wires of which both ends are adhered to electrodes; and at least one signal sensing part which is disposed in the vicinity of the nano wires on a surface of the solid substrate and to which glutamate oxidase to catalyze the oxidative reaction of glutamate is adhered.

In accordance with another aspect of the present invention, there is provided a method for manufacturing a biosensor for detecting glutamate, including the steps of: integrating nano wires on a surface of a solid substrate; coating electrodes with a polymer after forming the electrodes at both ends of each of the nano wires; adhering functional groups between the nano wires which is on the surface of the solid substrate; adhering glutaraldehyde to the functional groups on the surface of the solid substrate; and immobilizing glutamate oxidase, which is capable of catalyzing the oxidative reaction of monosodium glutamate, to glutaraldehyde.

Moreover, In accordance with another embodiment of the present invention, there is provided a method for detecting glutamate based on the bio sensor.

In the present invention, "nano wires" includes a hollow type nano tube, an inside-filled nano wire and a nano rod.

ADVANTAGEOUS EFFECTS

A biosensor for detecting glutamate according to the present invention can be manufactured with an arrangement in which the nano wire is selectively arranged on a solid substrate in a matrix. Since this biosensor can prevent the degradation of the nano wire in the electrical characteristic, it can sensitively detect glutamate even through a small amount thereof is contained in a food so that it can be effectively used in detecting the food additive existing in the processed foodstuffs. Moreover, since it is possible to minimize the size of the biosensor, it can be adhered to a personal digital assistant, a hand-held phone or a portable food additive detector.

BEST MODE FOR THE INVENTION

Figure 1:
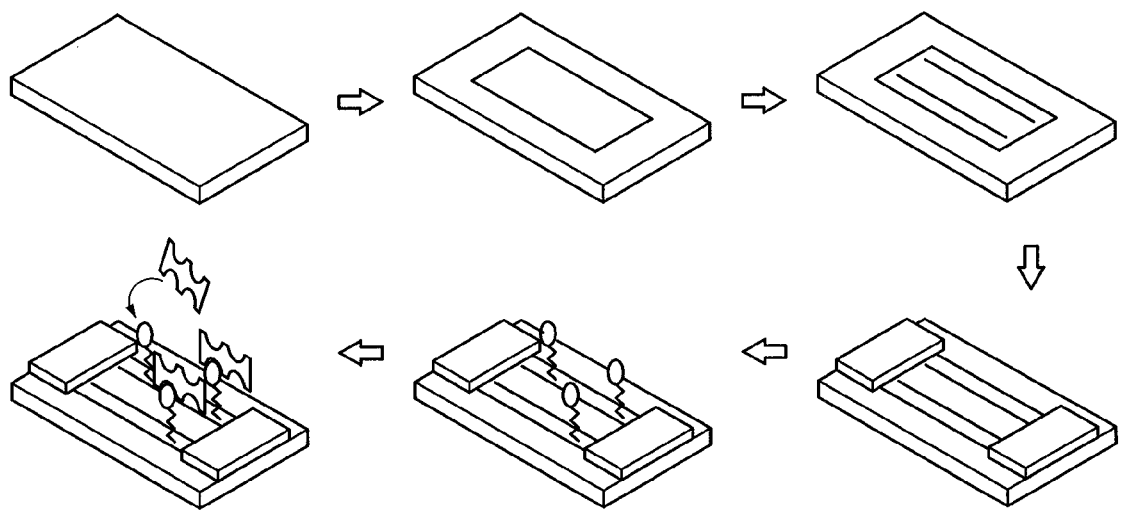
FIG. 1 is a schematic diagram illustrating a biosensor according to the present invention.

Hereinafter, the present invention will be described in detail.

A biosensor using a conventional nano wire has a structure in which a receptor capable of being bound to a target substance is directly immobilized on the nano wire. However, the biosensor according to the present invention is characterized in that a receptor is immobilized in the vicinity of the nano wires, i.e., on a surface of a substrate between one nano wire and the other one.

The biosensor for detecting glutamate according to the present invention includes a solid substrate, at least one signal transducer which is arranged in a matrix and has nano wires of which both ends are adhered to electrodes, and at least one signal sensing part which is disposed in the vicinity of the nano wires on a surface of the solid substrate and to which glutamate oxidase, as a receptor, to catalyze the oxidative reaction of glutamate is adhered.

In the present invention, glutamate is monosodium L-glutamate and L-glutamate. Monosodium L-glutamate to be detected in the present invention is called as monosodium glutamate. Monosodium L-glutamate is dissolved in an aqueous solution so that it separates into sodium ions and L-glutamate. Accordingly, the biosensor according to the present invention can ultimately detect a food additive of monosodium L-glutamate by using a material which selectively reacts only to L-glutamate.

The above-mentioned solid substrate is preferably a substrate which has an insulating surface, such as a silicon or glass substrate, and the silicon substrate typically includes, but not limited to, a silicon oxide film ($SiO_2$) in the present invention.

The biosensor for detecting monosodium glutamate according to the present invention includes the signal sensing part and the signal transducer disposed on the surface of the solid substrate. The signal sensing part is a portion where a physical or chemical change is caused by the reaction of the receptor or a biochemical substance having an ability to sense the target substance and the signal transducer is a portion where an quantitative analysis of the signal from the signal sensing part is made by using a physical or chemical conversion apparatus having electrodes, etc.

The signal transducer of the biosensor for detecting monosodium glutamate according to the present invention is made of the nano wires which are arranged on the surface of the solid substrate in the matrix and the electrodes are adhered to both ends of the nano wires. The electrodes, which connect the signal transducer to an external signal supplying circuit and a sensing circuit, function as contact junctions to make electrical characteristics observed. The physical and chemical reaction caused in the signal sensing part brings about the change of the electrical characteristic of the signal transducer and it is possible to sense this change through the adhesion junctions at an outside. Each of the electrodes consists of a double structure of a conductive metal and an adhesion metal and the electrodes can be successively deposited by an equipment such as a thermal evaporator, a sputter, or an E-beam evaporator, etc. The adhesion metal is in contact with the nano wire firstly and the conductive metal may be adhered to the adhesion metal when the adhesion metal has the strong binding force with the surface. It is preferable that a metal, which has the excellent electrical contact characteristic with the nano wire and the strong adhesion to the surface for the physical robustness, such as titanium or chrome, are preferably used as the adhesion metal. The conductive metal can be employed by a high conductivity metal without any limitation, especially Au in the preferred embodiment of the present invention.

Moreover, the signal sensing part of the biosensor for detecting glutamate according to the present invention is disposed in the vicinity of the signal transducer including the nano wires and the electrodes and glutamate oxidase, as a receptor, which is capable of being bound to the target substance of glutamate and catalyze the oxidative reaction of glutamate, is adhered to the signal sensing part.

Glutamate oxidase, as a receptor, is adhered to the function group on the surface of the solid substrate by glutaraldehyde. However, the adhesion of the enzyme is not limited to this method. The enzyme functions as a catalyst to create reactants by palpating the oxidation of glutamate. Since ammonia of the reactants changes the conductivity of the carbon nanotube, the enzyme can be immobilized on the surface of the substrate, directly to the nano wire, or on the electrodes.

The functional group connecting glutaraldehyde to the solid substrate is, but not limited to, at least one selected from the group consisting of an amine group, a carboxyl group and a thiol group.

The nano wires deposited on the signal transducer of the biosensor according to the present invention is, but not limited to, at least one selected from the group consisting of a carbon nanotube, a silicon nano wire, and a zinc oxide nano wire and a vanadium oxide nano wire.

More specifically, the biosensor for sensing glutamate according to the present invention will be described below referring to FIG. 2.

First, one or more signal transducers 102 exist on the solid substrate 107 and the signal transducers 102 include the carbon nanotubes 104 and the electrodes 105 which are disposed at both ends of the carbon nanotube 104. The electrodes 105 are coated with a polymer 106. The signal transducers 102 are arranged on the solid surface in a matrix and the signal sensing part 101 is provided by a portion in which the carbon nanotube 104 are not formed, that is, a portion between the signal transducers 102. The glutamate oxidase 103 is adhered to the signal transducers 102 by glutaraldehyde which is adhered to the functional groups.

Meanwhile, the present invention provides a method for manufacturing the biosensor. The method for manufacturing the biosensor includes the steps of: integrating nano wires on a surface of a solid substrate; coating electrodes with a polymer after forming the electrodes at both ends of each of the nano wires; adhering functional groups on the surface of the solid substrate between the nano wires; adhering glutaraldehyde, as a linker, to the functional groups on the surface of the solid substrate; and immobilizing glutamate oxidase, which is capable of being bound to glutamate and catalyze the oxidative reaction of glutamate, to glutaraldehyde.

To manufacture the biosensor according to the present invention, first, the nano wires are integrated on the surface of the solid substrate such as a silicon oxide film or a glass substrate. The integration of the nano wires on the surface of the substrate can be implemented by the general methods which are well known to those skilled in the art to which the subject pertains. Particularly, in the method for integrating the nano wires according to the preferred embodiment of the present invention, the surface of the solid substrate is patterned by a slippery molecular layer and the nano structure material to be adhered is then slid onto the surface of the solid substrate from the slippery molecular layer so that the nano wires are adhered directly on the surface of the solid substrate.

Next, the electrodes are deposited at both ends of each of the nano wires. The deposition of the electrodes is carried out by a thermal evaporator, an E-beam evaporator or a sputter which is typically used in manufacturing electrodes of semiconductor devices. The deposited electrodes are coated with the polymer in order to reduce a leakage current. After forming the signal transducers made of the nano wires and the electrodes, the functional groups are adhered on the surface of the solid substrate and between one nano wire and an adjacent nano wire and then glutaraldehyde, as a linker, is adhered to the functional groups. Finally, glutamate oxidase, as a receptor which is capable of being bound to the target substance of glutamate and catalyze the oxidative reaction of glutamate, is immobilized.

Glutamate oxidase, as an enzyme to dissociate glutamate, plays a role of a catalyst which is not chemically changed itself, but makes glutamate separate into by-products, α-ketoglutarate, hydrogen peroxide and ammonia. At this time, especially, ammonia among the different by-products diversifies the electrical characteristic of the nano wire and glutamate is detected through such a change.

Being different from the conventional biosensor, the biosensor according to the present invention is characterized in that the functional groups are selectively adhered on the surface of the solid substrate on which the nano wires are not integrated. In the present invention, in order to selectively adhere the functional groups on the surface of the solid substrate on which the nano wires are not integrated, a compound bearing a silane group is used. Especially, 3-aminopropyltriethoxysilane (APTES) is used in the present invention. If the ethoxylated group within the silane group meets with —OH on the silicon oxide film or the glass surface, the ethoxylated group is detached from the silane group and it is combined with the silicon surface with strong covalent bonds. In the cleaning process, molecules which are not combined with the covalent bonds are altogether gone away. Therefore, the functional groups are adhered to the surface in which the nano wires are not selectively integrated. Concretely, it is preferable that the substrate, on which the nano wires are integrated, is dipped in a compound having the silane group for 5 to 20 minutes. If the substrate is dipped for the above-mentioned time, the functional groups can be more selectively and effectively adhered to the surface on which the nano wires are not integrated.

Generally, the nano wires are classified into various kinds of chemical structures of the surface and these chemical structures are completely different from each other. For example, the carbon nanotube consists of the carbon lattice structure of a hexagon and the silicon nano wire is composed of a silicon crystalline structure. Besides, each of the nano wires, such as a zinc oxide nano wire, a vanadium oxide nano wire and so on, has a different chemical property of the surface. When the receptor capable of being bound additionally to the target substance is immobilized after various kinds of nano wires are integrated on the solid surface, a different chemical process has to be applied to each nano wire and this process has to satisfy the complicated conditions. That is, the receptor immobilization technique, in which the receptor is immobilized by the non-covalent bonds based on the hydrophobic interaction between a phenyl group or an alkyl group and the carbon nanotube or by the covalent bonds to attack a carboxyl group on the surface of the carbon nanotube, is used in case of the carbon nanotube. In case of a silicon nano wire, the silane group is used. This has a problem in that it takes a lot of time to immobilize the receptor after the integrated circuit processing in a mass product of the nano wires and the processes are very complicated. Moreover, a process of a specific nano wire can be very injurious to other nano wires. However, in the present invention, the receptors capable of being bound to the target substance to be sensed are not adhered directly to the nano wires, but immobilized in the vicinity of the nano wires, so that it is possible to immobilize the receptors regardless of the kinds of the nano wires. As a result, the present invention has the advantage of the cost-effectiveness in time and resources.

Hereinafter, the present invention is exemplarily illustrated with an embodiment.

However, the following embodiment exemplarily illustrates the present invention and the present invention is not restricted to the following embodiment.

Embodiment 1

Manufacturing Biosensor for Detecting Glutamate

A photoresist pattern is formed on a surface of a silicon oxide substrate by using the photolithography process. Thereafter, it is soaked in a solution in which octadecyl trichloro silane (hereinafter, referred to ad OTS) (sigma) and ethanol are mixed at a mixed ratio of 1:500 (volume ratio) and the OTS molecular layer is formed on the substrate surface.

Next, the substrate on which the molecular monolayer is formed is dipped in an acetone solution and the photoresist pattern is removed. The substrate is dipped in a carbon nanotube solution of o-dichlorobenzene and the carbon nanotubes are self-assembled on the substrate surface.

Titanium and then Au films are deposited on the carbon nanotubes of the substrate and the metals outside the electrode regions are removed by lift-off process. The electrodes are then coated with a polymer like SU-8.

Next, the substrate on which the carbon nanotubes are integrated is dipped in 3-aminopropyltriethoxysilane (APTES) (sigma) solution for 5 minutes and an amine group are selectively attached to the carbon nanotubes on the silicon substrate.

After glutaraldehyde, as a linker, is adhered to the substrate to which the amine group is adhered, the substrate is dipped in a glutamate oxidase solution so that the biosensor for detecting glutamate is finally manufactured by binding the amine group to the receptor of glutamate oxidase. More concretely, the amine groups are first created on the surface of the substrate by using 3-aminopropyltriethoxysilane and this substrate is dipped in a 2.5% glutaraldehyde aqueous solution for 1 to 3 hours. At this time, a —CHO group and the amine group of glutaraldehyde are bound with the covalent bond. By doing so, the CHO group is changed to the functional group or the CHO group can be immediately immobilized without the functional process of the amine group. At this time, trimethoxysilane aldehyde is used.

Thereafter, glutamate oxidase is dissolved in phosphate buffered saline of pH7.4, the enzyme solution is dropt on the sample in which the CHO group is immobilized, and the reaction is continuously carried out for 12 hours. In this process, the amine group in the amino acid sequence of the enzyme and the CHO group are bound with the covalent bonds.

Figure 2:
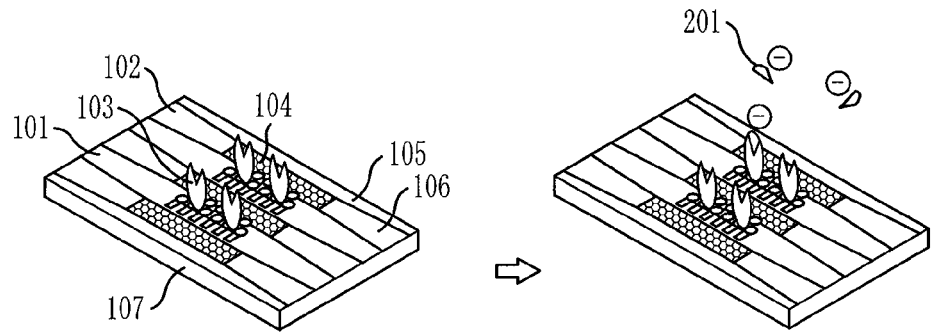
FIG. 2 is a schematic diagram illustrating a structure of the biosensor according to the present invention.

The biosensor manufacturing process is shown in FIG. 1 and the structure of the finally manufactured biosensor is shown in FIG. 2.

Example 1

Detecting Glutamate

The performance test of the biosensor for detecting glutamate, as manufactured in the embodiment 1, is executed.

After the buffer solution (PBS pH 7.4) is dropt on the conventional biosensor (control group) in which glutamate oxidase is not immobilized and the biosensor in which glutamate oxidase is immobilized according to the preferred embodiment 1 of the present invention, the voltage of 0.01V is applied to the electrodes disposed at both ends of each electrode of the substrates and a current is sampled according to the time. The results of the current variance with injection of glutamate (monosodium L-glutamate) and with no injection thereof are shown in FIGS. 3 and 4, respectively.

Figure 3:
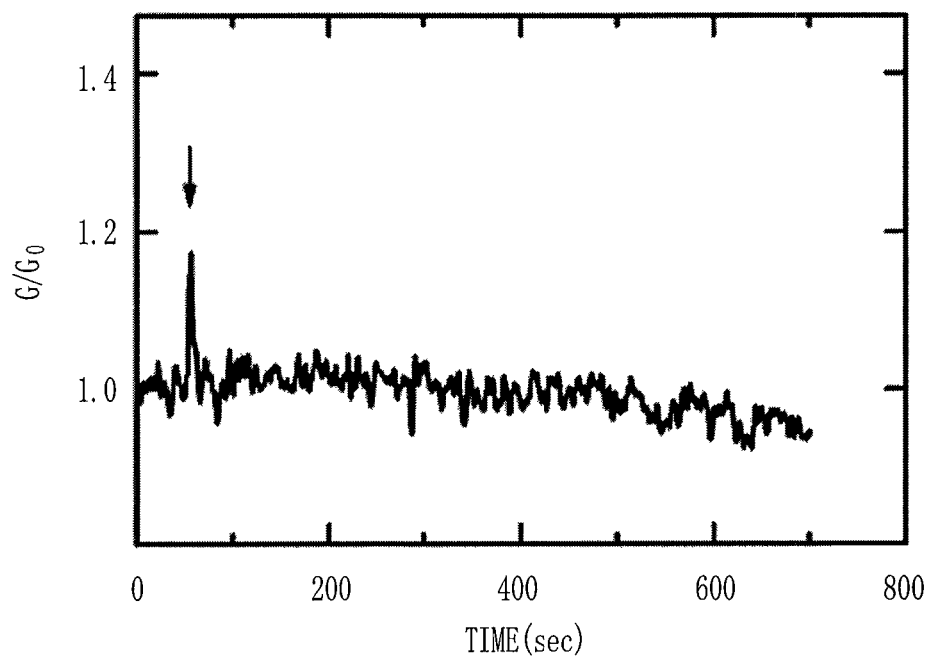
FIG. 3 is a graph illustrating a change of conductivity after administering monosodium L-glutamate to a conventional biosensor.

Referring to FIG. 3, the conventional biosensor in which glutamate oxidase is not immobilized has a constant current even if monosodium L-glutamate is applied to the biosensor and the time is sufficiently over.

Figure 4:
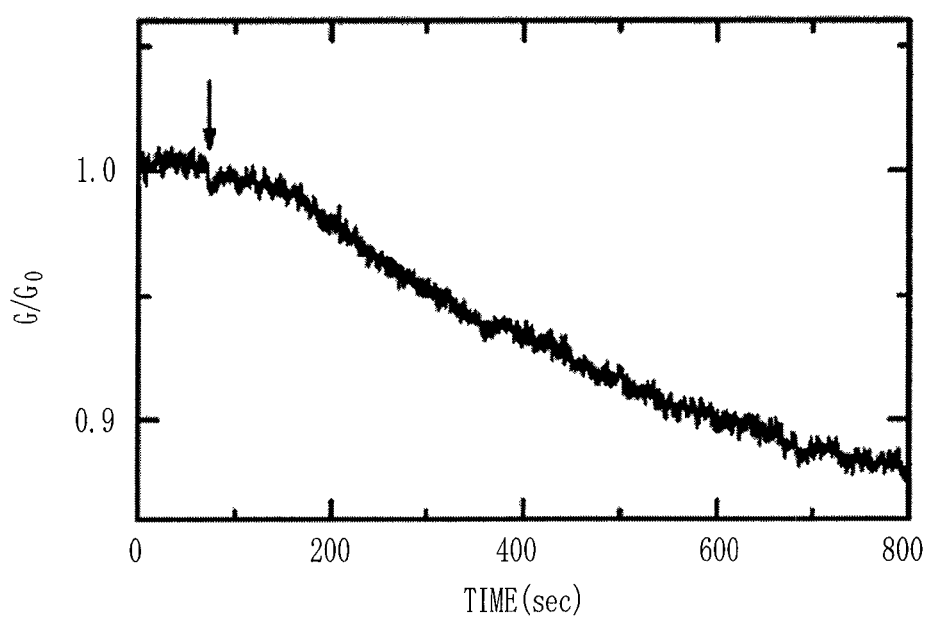
FIG. 4 is a graph showing a change of conductivity after administering the monosodium L-glutamate to the biosensor to which glutamate oxidase is immobilized according to the present invention.

However, referring to FIG. 4, the biosensor in which glutamate oxidase is immobilized according to the present invention shows a reduction of current after about 20 seconds in case of administrating monosodium L-glutamate of 5 mM. That is, glutamate can be effectively detected with a small amount thereof. Therefore, the high sensitivity of the biosensor of the present invention can be confirmed through FIG. 4.

What is claimed is:

1. A method for manufacturing a biosensor for detecting glutamate, comprising the steps of:
    integrating nano wires on a surface of a solid substrate;
    coating electrodes with a polymer after forming the electrodes at both ends of each of the nano wires;
    adhering a functional group on the surface of the solid substrate between the nano wires;
    adhering glutaraldehyde to the functional group on the surface of the solid substrate; and
    immobilizing glutamate oxidase, which is capable of being bound to monosodium glutamate and catalyze the oxidative reaction of glutamate, to glutaraldehyde.

2. The method of claim 1, wherein glutamate is monosodium glutamate and L-glutamate.

3. The method of claim 1, wherein the solid substrate is a silicon substrate or a glass substrate.

4. The method of claim 1, wherein the functional group is at least one selected from the group consisting of an amine group, a carboxyl group and a thiol group.

5. The method of claim 1, wherein the nano wire is at least one selected from the group consisting of a carbon nanotube, a silicon nano line, a zinc oxide nano wire and a vanadium oxide nano wire.

6. The method of claim 1, wherein the step of adhering the functional group on the surface of the solid substrate between the nano wires comprises dipping the substrate in a compound having a silane group for 5 to 20 minutes.

* * * * *